United States Patent [19]

Böhner

[11] 4,391,976
[45] Jul. 5, 1983

[54] PROCESS FOR PRODUCING ARYLSULFAMATES

[75] Inventor: Beat Böhner, Binningen, Switzerland

[73] Assignee: Ciba-Geigy Corporation, Ardsley, N.Y.

[21] Appl. No.: 313,064

[22] Filed: Oct. 19, 1981

[51] Int. Cl.³ .................. C07D 251/46; C07D 251/42; C07D 239/42; C07D 239/47

[52] U.S. Cl. .................................... 544/211; 544/321; 544/332

[58] Field of Search ........................ 544/211, 321, 332

[56] References Cited

U.S. PATENT DOCUMENTS 4,191,553 3/1980 Reap ................................... 544/211

OTHER PUBLICATIONS

Lohaus *Chem. Ber.* 105, 2791 (1972).

*Primary Examiner*—John M. Ford
*Attorney, Agent, or Firm*—Karl F. Jorda

[57] ABSTRACT

A process for producing an N-(heterocyclo-aminocarbonyl)-arylsulfamate of the general formula I

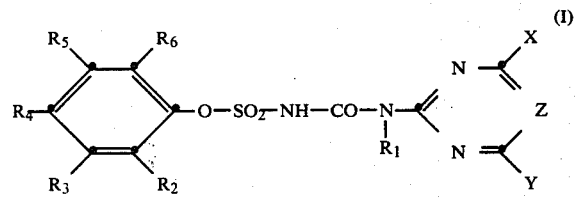

wherein
$R_1$ is hydrogen, methoxy or $C_1$-$C_3$-alkyl,
$R_2$ is hydrogen, fluorine, chlorine, bromine, nitro, $CF_3$, $C_1$-$C_4$-alkyl, $C_1$-$C_4$-alkoxy or $C_1$-$C_4$-alkoxycarbonyl,
$R_3$ is hydrogen, fluorine, chlorine, bromine, methyl or $C_1$-$C_4$-alkoxy,
$R_4$ is hydrogen, fluorine, chlorine, bromine, nitro, cyano, $C_1$-$C_4$-alkyl, $C_1$-$C_4$-alkoxy or $C_1$-$C_4$-alkoxycarbonyl,
$R_5$ is hydrogen, fluorine, chlorine, bromine, nitro or $CF_3$,
$R_6$ is hydrogen, fluorine, chlorine, bromine, $C_1$-$C_4$-alkyl or $C_1$-$C_4$-alkoxy,
X is $C_1$-$C_2$-alkyl, $C_1$-$C_3$-alkoxy, $C_1$-$C_2$-alkylthio, methoxymethyl, methoxyethyl, $CF_3$ or chlorine,
Y is $C_1$-$C_2$-alkyl, $C_1$-$C_3$-alkoxy, $C_1$-$C_2$-alkylthio, methoxymethyl or methoxyethyl, and
Z is the methine group or nitrogen, which process comprises adding, in an inert organic solvent, chlorosulfonylisocyanate of the formula III

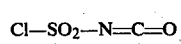

to an aminoheterocyclic compound of the formula II

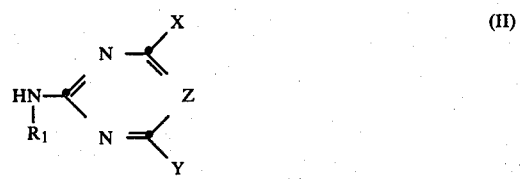

wherein $R_1$, X, Y and Z have the meanings defined under the formula I; and subsequently reacting this mixture, optionally with the addition of an agent binding hydrogen chloride, with a phenol of the formula IV

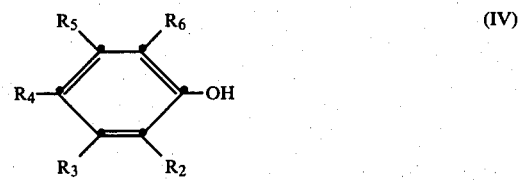

wherein $R_2$ and $R_3$ have the meanings given under the formula I.

11 Claims, No Drawings

PROCESS FOR PRODUCING ARYLSULFAMATES

The present invention relates to a novel process for producing N-(heterocyclo-aminocarbonyl)-arylsulfamates.

N-(Heterocyclo-aminocarbonyl)-arylsulfamates are known as being herbicides for pre- and post-emergence application. Herbicidal active substances of this type, their production, compositions containing them and the use thereof are described in the U.S. Pat. No. 4,191,553.

According to the production process described in the U.S. Pat. No. 4,191,553, the herbicidal N-(heterocyclo-aminocarbonyl)-arylsulfamates are obtained by firstly refluxing phenols with chlorosulfonylisocyanate in toluene or xylene for 1½ to 2 hours, and isolating the intermediate reaction product. The formed aryloxysulfonylisocyanate is reacted, in a second reaction step, with a triazinyl- or pyrimidinylamine. The known 2-stage process is disadvantageous in that, with the formation of the aryloxysulfonyl-isocyanate-starting product by heating at temperatures of 110°–140° C., there can always occur, as by-products, 3-oxo-2,3-dihydro-4,1,2-benzoxathiazine-1,1-dioxide derivatives when the employed phenols have a free ortho-position [cp. Chem. Ber. 105, 2791 (1972)]. Furthermore, it is possible under the applied reaction conditions for substituents of the phenol ring which are sensitive to acid to become decomposed by the formed hydrogen chloride. And, finally, the performed process is uneconomical also in view of the necessary heating of the reaction mixture in the first step.

The object of the present invention was thus to avoid the disadvantages of the known process, and to provide a process by which N-(heterocycloaminocarbonyl)-arylsulfamates can be produced on a commercial scale in a simple, unequivocal and economical manner.

According to the process of the invention, the herbicidal N-(heterocyclo-aminocarbonyl)-arylsulfamates of the general formula I

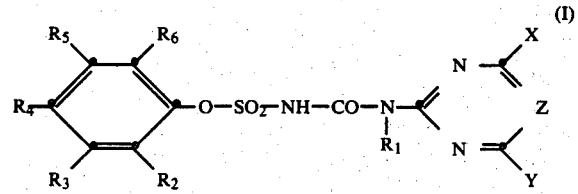

wherein $R_1$ is hydrogen, methoxy or $C_1$–$C_3$-alkyl, $R_2$ is hydrogen, fluorine, chlorine, bromine, nitro, $CF_3$, $C_1$–$C_4$-alkyl, $C_1$–$C_4$-alkoxy or $C_1$–$C_4$-alkoxycarbonyl, $R_3$ is hydrogen, fluorine, chlorine, bromine, methyl or $C_1$–$C_4$-alkoxy, $R_4$ is hydrogen, fluorine, chlorine, bromine, nitro, cyano, $C_1$–$C_4$-alkyl, $C_1$–$C_4$-alkoxy or $C_1$–$C_4$-alkoxycarbonyl, $R_5$ is hydrogen, fluorine, chlorine, bromine, nitro or $CF_3$, $R_6$ is hydrogen, fluorine, chlorine, bromine, $C_1$–$C_4$-alkyl or $C_1$–$C_4$-alkoxy, X is $C_1$–$C_2$-alkyl, $C_1$–$C_3$-alkoxy, $C_1$–$C_2$-alkylthio, methoxymethyl, methoxyethyl, $CF_3$ or chlorine, Y is $C_1$–$C_2$-alkyl, $C_1$–$C_3$-alkoxy, $C_1$–$C_2$-alkylthio, methoxymethyl or methoxyethyl, and Z is the methine group or nitrogen, are obtained by adding, in a single-vessel process, in an inert organic solvent, chlorosulfonylisocyanate of the formula III

to an aminoheterocyclic compound of the formula II

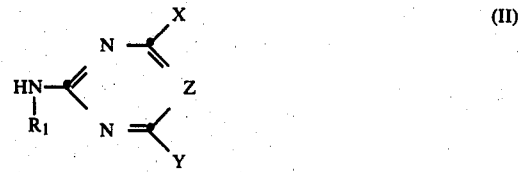

wherein $R_1$, X, Y and Z have the meanings defined under the formula I; and subsequently reacting this mixture, optionally with the addition of an agent binding hydrogen chloride, with a phenol of the formula IV

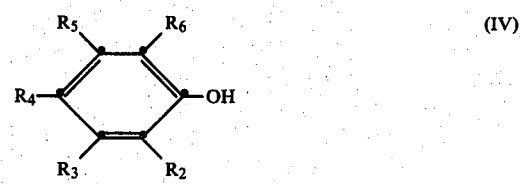

wherein $R_2$ and $R_3$ have the meanings given under the formula I.

The process according to the invention is exothermic, so it can therefore be necessary to cool the reaction vessel. The process is carried out at temperatures of between −10° C. and +80° C., preferably between 0° C. and 40° C.

Suitable inert organic solvents which can be used are: hydrocarbons, such as benzene, toluene, xylene or cyclohexane; chlorinated hydrocarbons, such as methylene chloride, chloroform, carbon tetrachloride or chlorobenzene, and ethers, such as diethyl ether, dimethoxyethane, diethylene glycol-dimethyl ether, tetrahydrofuran or dioxane. Preferred solvents are cyclic or polyvalent ethers, such as tetrahydrofuran, dioxane or dimethoxyethane.

Suitable agents binding hydrogen chloride are carbonates and hydrogen carbonates of alkali metals and alkaline-earth metals, such as sodium and potassium carbonate and sodium and potassium hydrogen carbonate, or tertiary amines, such as pyridine, 4-dimethylaminopyridine, quinoline, isoquinoline, quinuclidine, triethylamine or trimethylamine.

Chlorosulfonylisocyanate is used according to the invention in an equimolar amount or in a slight excess. It is advantageous to use 1.0 to 1.3 mols of chlorosulfonylisocyanate per mol of aminoheterocyclic compound. The amount preferably used in 1.0 to 1.2 mols, depending on the degree of purity of the chlorosulfonylisocyanate. On account of the high reactivity of the chlorosulfonylisocyanate, it is of advantage to use solvents which are free from water and alcohol.

In a preferred embodiment of the process according to the invention, the heterocycloamine of the formula II is suspended in absolute dioxane, and at 5°–10° C. are added, with cooling, 1.0–1.2 mols of chlorosulfonylisocyanate per mol of aminoheterocyclic compound. To the formed clear solution is added 0.9–1.0 mol of the phenol of the formula IV per mole of aminoheterocyclic compound. There is optionally added to the solution 1 mol of triethylamine in such a manner that the temperature of the reaction mixture does not exceed 25° C. After the reaction mixture has been stirred at 20°–25° C. until the reaction of the starting materials is completed, the solvent, after filtration, is evaporated off, and the product is obtained by crystallisation of the residue.

It is possible by the process according to the invention to produce N-(heterocycloamino-carbonyl)-arylsulfamates on a commercial scale in a simple, clear and economical manner. The process avoids the isolation of an intermediate, a step which is necessary in the known process, and requires no heating of the reaction mixture. Also avoided by the process of the invention is the formation to by-products, even when the ortho-position of the phenol ring is unoccupied and when the phenol ring carries substituents sensitive to acid, because the process according to the invention can be performed at considerably lower temperatures.

By the reaction of chlorosulfonylisocyanate (III) with an amine of the formula II intermediates of the formula V are formed

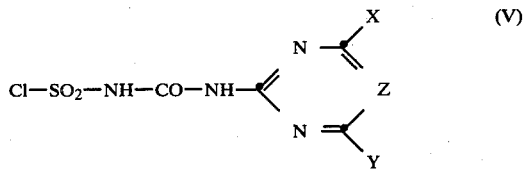

(V)

wherein X, Y and Z have the meaning given under the formula I.

These intermediates of the formula V are part of the invention.

Examples of the intermediates of the formula V are listed below.

N-(4-methoxy-6-methyl-1,3,5-triazin-2-yl)-N-chlorosulfonylurea, mp. 79° C. (dec.),
N-(4,6-dimethyl-1,3,5-triazin-2-yl)-N'-chlorosulfonylurea,
N-(4,6-dimethoxy-1,3,5-triazin-2-yl)-N'-chlorosulfonylurea,
N-(4-methoxy-6-methyl-pyrimidin-2-yl)-N'-chlorosulfonylurea,
N-(4,6-dimethoxy-pyrimidin-2-yl)-N'-chlorosulfonylurea,
N-(4,6-dimethyl-pyrimidin-2-yl)-N'-chlorosulfonylurea,
N-(4-methyl-6-methylthio-1,3,5-triazin-2-yl)-N'-chlorosulfonyl-urea,
N-(4-methoxymethyl-6-methyl-1,3,5-triazin-2-yl)-N'-chlorosulfonyl-urea,
N-(4-ethyl-6-methoxy-pyrimidin-2-yl)-N'-chlorosulfonyl-urea,
N-(4-methoxy-6-trifluoromethyl-1,3,5-triazin-2-yl)-N'-chlorosulfonyl-urea and
N-(4-chloro-6-methyl-pyrimidin-2-yl)-N'-chlorosulfonyl-urea.

The intermediate compounds of the formula V can be obtained from a reaction which is carried out according to the first part of the inventive process and isolation of the formula V compounds by evaporating off the solvent.

Instead of isolating the intermediates it is particularly preferable to produce these compounds in situ and to directly convert them to the end products of the formula I by adding phenols of the formula IV thereto according to the single vessel process of the invention.

The process according to the invention is further illustrated by the following Examples.

EXAMPLE 1

N-[(4-Methoxy-6-methyl-1,3,5-triazin-2-yl)aminocarbonyl]-O-phenylsulfamate

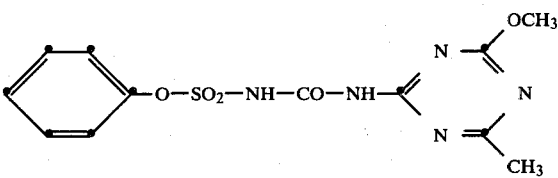

8.1 g (57.5 mmols) of chlorosulfonylisocyanate are added dropwise to a suspension, cooled to 5° C., of 7.0 g (50 mmols) of 2-amino-4-methoxy-6-methyl-1,3,5-triazine in 100 ml of abs. dioxane. When a clear solution has formed after about 10 minutes, 4.7 g (50 mmols) of phenol are added, as a result of which the temperature of the solution rises to 8° C. There are subsequently added dropwise to the solution, with slight cooling, 6.9 ml (50 mmols) of triethylamine in such a manner that the temperature of the reaction mixture does not exceed 25° C. After 16 hours of stirring at room temperature, the suspension is filtered through a short silica gel column. Concentration by evaporation of the clear yellow solution produces 12.5 g (74%) of N-[(4-methoxy-6-methyl-1,3,5-triazin-2-yl)-amino-carbonyl]-O-phenylsulfamate, which yields, after recrystallisation from an ether/benzine mixture, colourless crystals, m.p. 152°–153° C.

EXAMPLE 2

N-[(4,6-Dimethyl-pyrimidin-2-yl)-amino-carbonyl]-O-(2-chlorophenyl)-sulfamate

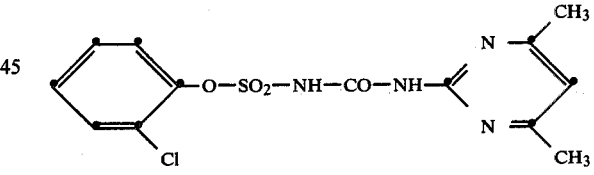

To a slightly cloudy solution, cooled to 5°–10° C., of 3.7 g (30 mmols) of 2-amino-4,6-dimethyl-pyrimidine in 25 ml of absolute dioxane are added dropwise 3.1 ml (35.4 mmols) of chlorosulfonylisocyanate. Immediately after the addition of the chlorosulfonylisocyanate, 2.9 ml (27.5 mmols) of 2-chlorophenol are added to the formed clear solution. After a stirring time of 16 hours and concentration by evaporation, the oily residue is taken up in a small amount of methylene chloride, and the suspension is filtered through a short silica gel column. The solution is concentrated by evaporation to obtain 8.2 g (76.6%) of N-[(4,6-dimethyl-pyrimidin-2-yl)aminocarbonyl]-O-(2-chlorophenyl)-sulfamate, which, after recrystallisation from an ether/benzine mixture, yields colourless crystals, m.p. 145°–147° C.

Further compounds of the formula I can be obtained in an analogous manner, for example those listed in the U.S. Pat. No. 4,191,553.

What is claimed is:

1. A process for producing an N-(heterocyclo-aminocarbonyl)-arylsulfamate of the formula I

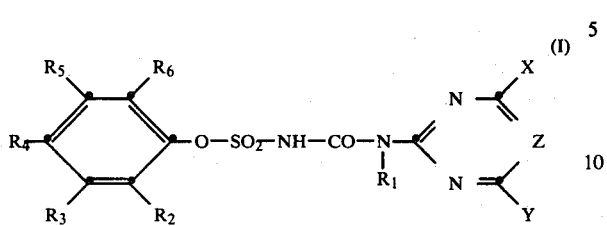

wherein $R_1$ is hydrogen, methoxy or $C_1$-$C_3$-alkyl, $R_2$ is hydrogen, fluorine, chlorine, bromine, nitro, $CF_3$, $C_1$-$C_4$-alkyl, $C_1$-$C_4$-alkoxy or $C_1$-$C_4$-alkoxycarbonyl, $R_3$ is hydrogen, fluorine, chlorine, bromine, methyl or $C_1$-$C_4$-alkoxy, $R_4$ is hydrogen, fluorine, chlorine, bromine, nitro, cyano, $C_1$-$C_4$-alkyl, $C_1$-$C_4$-alkoxy or $C_1$-$C_4$-alkoxycarbonyl, $R_5$ is hydrogen, fluorine, chlorine, bromine, nitro or $CF_3$, $R_6$ is hydrogen, fluorine, chlorine, bromine, $C_1$-$C_4$-alkyl or $C_1$-$C_4$-alkoxy, X is $C_1$-$C_2$-alkyl, $C_1$-$C_3$-alkoxy, $C_1$-$C_2$-alkylthio, methoxymethyl, methoxyethyl, $CF_3$ or chlorine, Y is $C_1$-$C_2$-alkyl, $C_1$-$C_3$-alkoxy, $C_1$-$C_2$-alkylthio, methoxymethyl or methoxyethyl, and Z is the methine group or nitrogen, which process comprises adding, in an inert organic solvent, chlorosulfonylisocyanate of the formula III

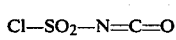

(III)

to an aminoheterocyclic compound of the formula II

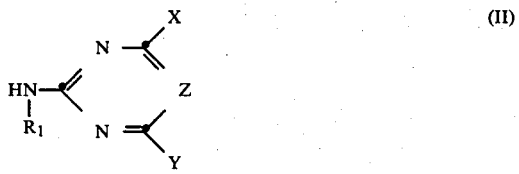

wherein $R_1$, X, Y and Z have the meanings defined under the formula I; and subsequently reacting this mixture, optionally with the addition of an agent binding hydrogen chloride, with a phenol of the formula IV

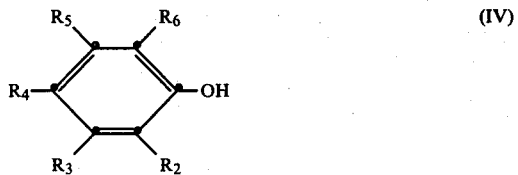

wherein $R_2$ and $R_3$ have the meanings given under the formula I.

2. A process according to claim 1, wherein the reaction temperature is maintained between $-10°$ C. and $+80°$ C.

3. A process according to claim 2, wherein the reaction temperature is between $0°$ C. and $+40°$ C.

4. A process according to claim 1, wherein cyclic or polyvalent ethers are used as solvent.

5. A process according to claim 4, wherein the solvent is tetrahydrofuran, dioxane or dimethoxyethane.

6. A process according to claim 1, performed in the presence of an agent binding hydrogen chloride, in which process carbonates or hydrogen carbonates of alkali metals or alkaline-earth metals, or tertiary amines, are used as binding agents.

7. A process according to claim 6, wherein sodium or potassium carbonate, sodium or potassium hydrogen carbonate, pyridine or triethylamine are used.

8. A process according to claim 1, wherein no agent binding hydrogen chloride is used.

9. A process according to claim 1, wherein 1.0 to 1.3 mols of chlorosulfonylisocyanate per mol of the aminoheterocyclic compound are used.

10. A process according to claim 9, wherein 1.0 to 1.2 mols of chlorosulfonylisocyanate are used.

11. A process according to claim 1, which process comprises suspending the heterocycloamine of the formula II in absolute dioxane, adding at $5°$-$10°$ C., with cooling, 1.0 to 1.2 mols of chlorosulfonylisocyanate per mol of amine, introducing into the formed clear solution 0.9 to 1.0 mol of the phenol of the formula IV per mol of the aminoheterocyclic compound, optionally adding 1 mol of triethylamine in such a manner that the temperature of the reaction mixture does not exceed $25°$ C., subsequently stirring the reaction mixture at $20°$-$25°$ C. until the reaction of the starting materials is completed, filtering the reaction mixture, concentrating the filtrate by evaporation, and finally isolating the product by crystallisation.

* * * * *